US010863978B2

(12) United States Patent
Breslich

(10) Patent No.: US 10,863,978 B2
(45) Date of Patent: Dec. 15, 2020

(54) SUTURE TAPE CONSTRUCT FOR PROVIDING ANCHOR WITH NON-SLIDING SUTURE TAPE

(71) Applicant: ConMed Corporation, Utica, NY (US)

(72) Inventor: Grady Breslich, Bradenton, FL (US)

(73) Assignee: ConMed Corporation, Utica, NY (US)

( * ) Notice: Subject to any disclaimer, the term of this patent is extended or adjusted under 35 U.S.C. 154(b) by 62 days.

(21) Appl. No.: 15/390,969

(22) Filed: Dec. 27, 2016

(65) Prior Publication Data
US 2017/0181739 A1 Jun. 29, 2017

Related U.S. Application Data

(60) Provisional application No. 62/271,401, filed on Dec. 28, 2015.

(51) Int. Cl.
*A61B 17/04* (2006.01)
*A61B 17/06* (2006.01)

(52) U.S. Cl.
CPC .... *A61B 17/0401* (2013.01); *A61B 17/06166* (2013.01); *A61B 2017/0403* (2013.01); *A61B 2017/044* (2013.01); *A61B 2017/0406* (2013.01); *A61B 2017/0412* (2013.01); *A61B 2017/0414* (2013.01); *A61B 2017/0464* (2013.01); *A61B 2017/06176* (2013.01)

(58) Field of Classification Search
CPC ................ A61B 17/0401; A61B 17/04; A61B 17/06166; A61B 2017/0403; A61B 2017/0406; A61B 2017/06176; A61F 2/0811
See application file for complete search history.

(56) References Cited

U.S. PATENT DOCUMENTS

| 5,540,703 A | 7/1996 | Barker, Jr. et al. |
| 8,795,334 B2 | 8/2014 | Astorino et al. |

(Continued)

FOREIGN PATENT DOCUMENTS

WO 2012/151592 11/2012

OTHER PUBLICATIONS

International Search Report Form PCT/ISA/220, International Application No. PCT/US2016/68664, pp. 1-14, dated Jun. 12, 2017.

(Continued)

*Primary Examiner* — Sarah A Simpson
(74) *Attorney, Agent, or Firm* — Bond, Schoeneck & King, PLLC; Frederick J. M. Price

(57) ABSTRACT

A suture tape construct having a first section formed from a fibrous filament that extends from a first end to a second end and has a pair of a one-way protrusions extending therefrom. An anchor is positioned along the suture construct and, when the construct is deployed, is captured between the protrusions. The anchor may be a second section formed from braided suture material that is woven about the first section. The braided suture material can be deployed to form an all suture anchor while protrusions extending from the suture anchor proximately to the location of the deployed suture anchor prevent movement of the second section relative to the first section, thus forming a non-sliding suture tape anchored by the deployed braided material. The anchor may be a threaded anchor having an eyelet that is captured between the protrusions.

13 Claims, 7 Drawing Sheets

(56) References Cited

U.S. PATENT DOCUMENTS

| | | | |
|---|---|---|---|
| 9,078,651 B2 | 7/2015 | Astorino et al. | |
| 9,370,352 B2 | 6/2016 | Astorino et al. | |
| 9,888,997 B2 * | 2/2018 | Dreyfuss et al. | A61F 2/0811 606/232 |
| 2012/0101526 A1 * | 4/2012 | Bennett | A61B 17/0401 606/232 |
| 2012/0290004 A1 * | 11/2012 | Lombardo | A61B 17/0401 606/232 |
| 2014/0371792 A1 * | 12/2014 | Beck | A61B 17/0401 606/232 |

OTHER PUBLICATIONS

Ronald Glousman, M.D. and Nicholas Sgaglione, M.D., Labral Repair, JuggerKnot Soft Anchor brochure, 2010, 2011, 12 pages.

* cited by examiner

SUTURE TAPE CONSTRUCT FOR PROVIDING ANCHOR WITH NON-SLIDING SUTURE TAPE

CROSS REFERENCE TO RELATED APPLICATIONS

The present application relates and claims priority to U.S. Provisional Application Ser. No. 62/271,401 filed Dec. 28, 2015, the entirety of which is hereby incorporated by reference.

BACKGROUND OF THE INVENTION

1. Field of the Invention

The present invention relates to sutures and, more specifically, to a suture construct having non-sliding suture tape capturing a suture anchor.

2. Description of the Related Art

In soft tissue to bone repair procedures, such as rotator cuff repair, round sutures have commonly be used to hold soft tissue to bone in surgical procedures. An increasingly common practice, however, is to use what is referred to as suture tape, a generally flat material of woven fibers. Suture tape is considered advantageous for use in certain procedures such as rotator cuff repairs because it can promote increased tissue-to-bone contact area and can more evenly distribute pressure compared to round suture. A drawback of using suture tape is that knots formed from suture tape are larger than knots of round suture and thus are often avoided to reduce the chance of post-operative pain.

The double row rotator cuff repair is a common repair technique used to fix soft tissue to bone. In the repair, a suture anchor is placed at the medial row and two limbs of sliding #2 suture associated with the anchor are passed through the tissue and then tied together to create a horizontal mattress stich. The non-sliding tails of these stiches are then fixed to knotless anchors placed at the lateral row. Non-sliding sutures are generally preferred over sliding sutures for use with knotless anchors because non-sliding sutures do not require additional steps to maintain tension on the suture and reduce the risk of cutting though the tissue with a sawing effect as the suture slides though the tissue. If a double row repair is attempted with suture tape, however, the surgeon must either tie a horizontal mattress stitch with the suture tape, thus leaving a large irritating knot, or avoid the use of horizontal mattress stitch, thus leaving the suture free to slide and requiring additional steps that could potentially cause damage. Thus, there is a need for a non-sliding suture tape construct that can be used with a suture anchor at the medial row in a double row rotator cuff repair without forming large, irritating knots or requiring additional steps that could cause damage.

BRIEF SUMMARY OF THE INVENTION

Embodiments of the present invention include a suture anchor having a first section that extends from a first end to a second end, a second section woven about the first section between the first end and the second end and moveable between an extended position and a deployed position, and a pair of protrusions extending from the first section and positioned to allow movement of the second section from the extended position to the deployed position and to prevent movement of the second section from the deployed position to the extended position. The first section comprises suture tape and the second section is braided suture material to form an all-suture anchor. However, in alternative embodiments, the first section may be comprised of any type of flexible strands to hold soft tissue to bone, such as suture tape, round #2 suture, and monofilament suture, for example. Additionally, as an all suture anchor, the second section can also be embodied in other forms of objects to provide fixation to bone, such as flat woven material, with or without cannulation, and an eyelet or other ridged hole, including a revo-style eyelet and a crossFT® knotless style eyelet, for example. The protrusions may be suture woven into the suture tape of the first section. The suture anchor is deployed by inserting the anchor into a hole in a bone and pulling the first and second ends of the first section until the second section moves from the extended position to the deployed position. The protrusions trap the deployed braided material therebetween and prevent any movement of the suture tape relative to the deployed braided material.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
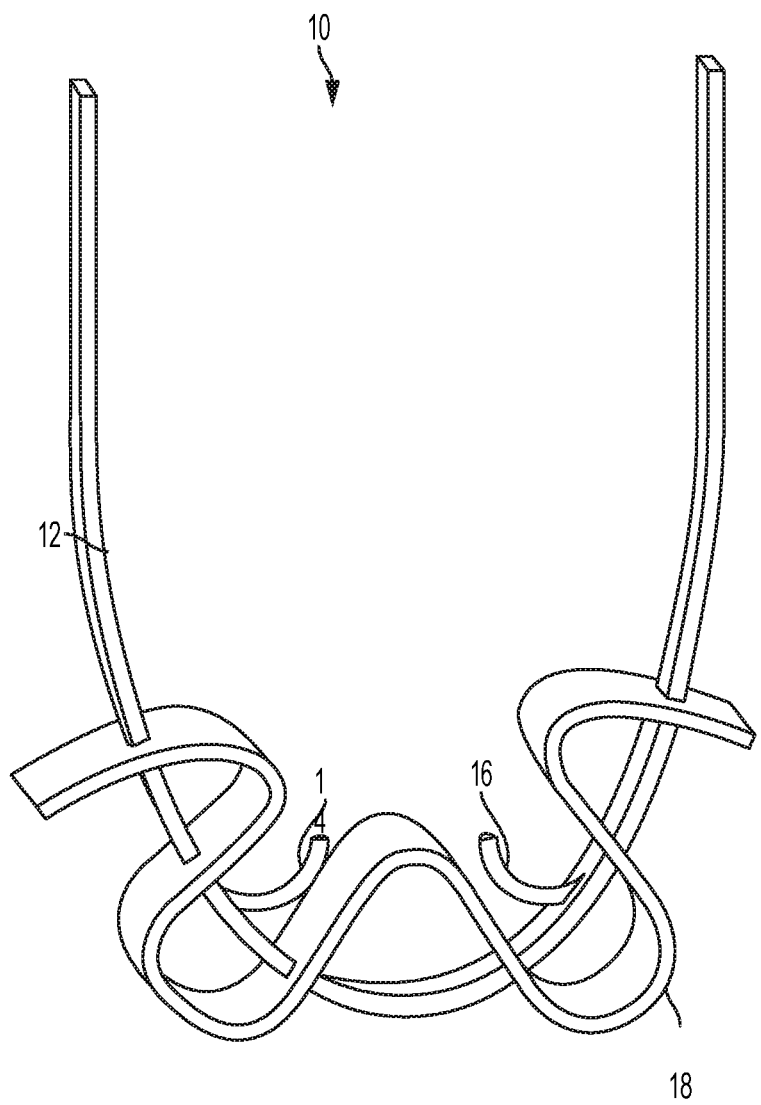
FIG. 1 is a schematic of a suture tape construct in an un-deployed configuration according to the present invention.

Referring now to the drawings, wherein like reference numerals refer to like parts throughout, there is seen in FIG. 1 a non-sliding suture construct 10 comprising a length of fibrous filament (which can be suture tape) 12 having a pair of protrusions 14 and 16 extending outwardly therefrom. A length of flat braided material 18 serving as a suture anchor is positioned along fibrous filament 12, i.e., fibrous filament 12 has been woven through braided material 18. For example, material 18 may be folded several times with fibrous filament 12 passing through each fold. In the depicted embodiment, braided material 18 has six punctures to receive suture fibrous filament 12; however, four punctures or eight punctures can be used (or any other number of punctures can be used as may be required for application of the non-sliding suture construct, as should be appreciated by a person of ordinary skill in the art in conjunction with a review of this disclosure). In accordance with an embodiment, flat braided material 18 may also be tubular (has a lumen). Further, in one embodiment, neither material 18 nor fibrous filament 12 has any knots, allowing free sliding of 18 over 12 (except for back over protrusions 14 and 16, described below).

Protrusions 14 and 16 may be formed from round #2 sutures that are partially woven into fibrous filament 12 so that the portion of protrusions 14 and 16 that extend from fibrous filament 12 form barbs that are angled toward the free ends of fibrous filament 12. The protrusions 14 and 16 can be formed separate from suture fibrous filament 12 or integrally with suture fibrous filament 12. In one embodiment where the protrusions 14 and 16 are integrally formed with suture fibrous filament 12, suture fibrous filament 12 is woven over the protrusion 14 and 16, which are pulled out of suture fibrous filament 12. In another embodiment, suture fibrous filament 12 is double backed into itself and exits itself to become protrusions 14 and 16.

Figure 2:
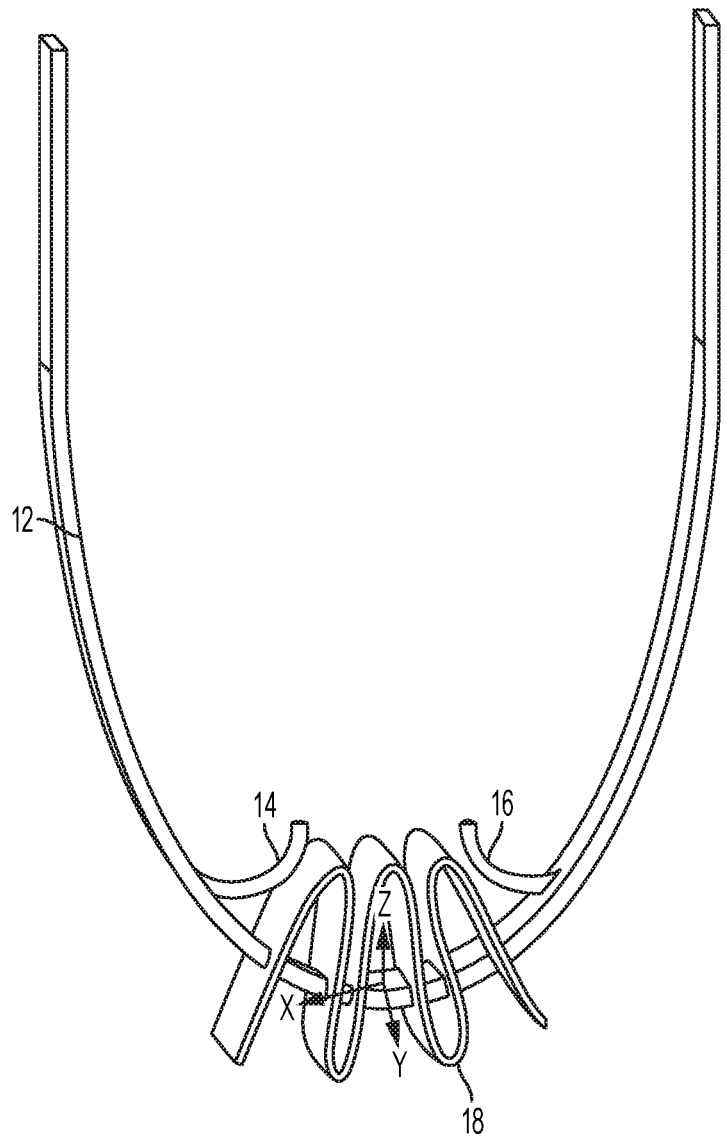
FIG. 2 is a schematic of a suture tape construct in a deployed configuration according to the present invention.

As stated above, protrusions 14 and 16 form barbs angled toward the free ends of fibrous filament 12. Protrusions 14 and 16 are thus configured to allow material 18 to pass thereover in a single direction, i.e., material 18 is free to transition from an extended un-deployed configuration as seen in FIG. 1 to a deployed configuration as seen in FIG. 2 by sliding over protrusions 14 and 16. The angling of protrusions 14 and 16 relative to fibrous filament 12 and braided material 18 prevents braided material 18 from sliding over protrusions 14 and 16 once braided material 18 is in the deployed configuration of FIG. 2.

Figure 7:
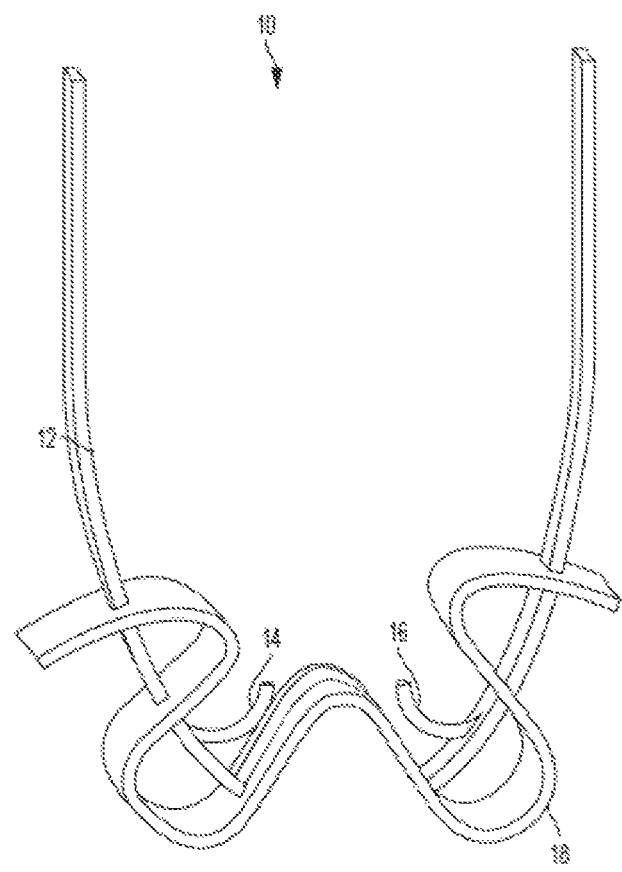
FIG. 7 is a schematic of an alternative embodiment of a suture tape construct in an un-deployed configuration according to the present invention.

Referring briefly to FIG. 7, there is seen an alternative embodiment of suture tape construct 10 in an un-deployed configuration. In the depicted embodiment, braided material 18 comprises a lumen extending through a portion of braided material 18 between protrusions 14 and 16. As shown, suture fibrous filament 12 is not only woven through braded material 18, but is also extended through the lumen portion.

The configuration of suture construct 10 illustrated in FIG. 2 provides an all-suture anchor that, when deployed inside a hole formed in a bone, may be used for a soft tissue to bone repair procedure, such as a double rotator cuff repair. Suture construct 10 may be deployed into a hole formed in bone with an installation device, such as that shown in FIG. 5 of U.S. Patent Publication No. 2012/0290004, which is incorporated herein by reference along with the related description in its entirety. Once braided material 18 has been shifted in the deployed configuration of FIG. 2, protrusions 14 prevent any further movement of material 18 relative to fibrous filament 12, thereby providing a non-sliding arrangement where fibrous filament 12 is fixed relative to material 18. Additionally, in the deployed configuration, braided material 12 between protrusions 14 and 16 can expand freely into the space within the bone, such as shown in FIG. 6 of U.S. Patent Publication No. 2012/0290004, which is incorporated herein by reference along with the related description in its entirety.

Figure 3:
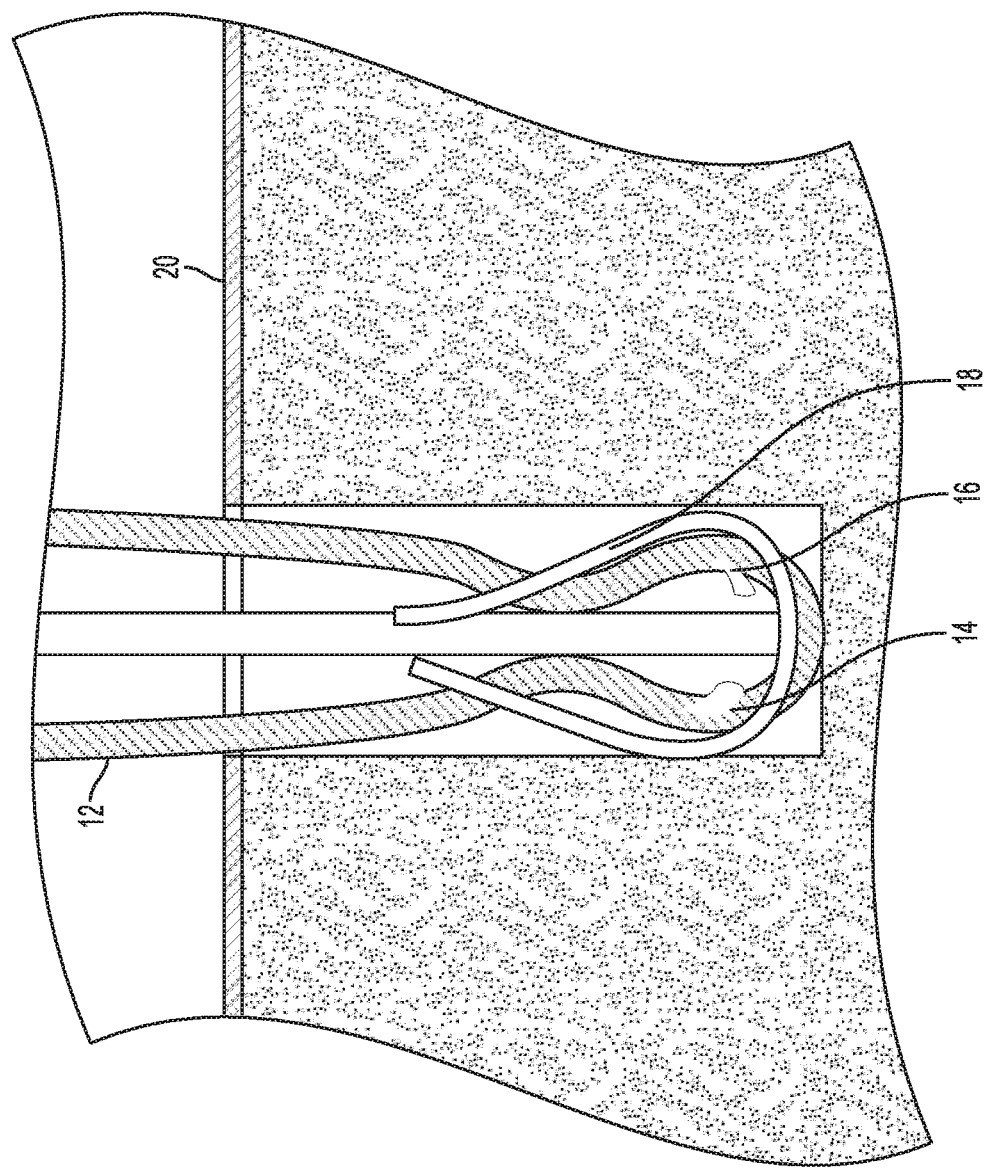
FIG. 3 is a schematic of a suture tape construct positioned in the bone of a subject prior to deployment.
Figure 4:
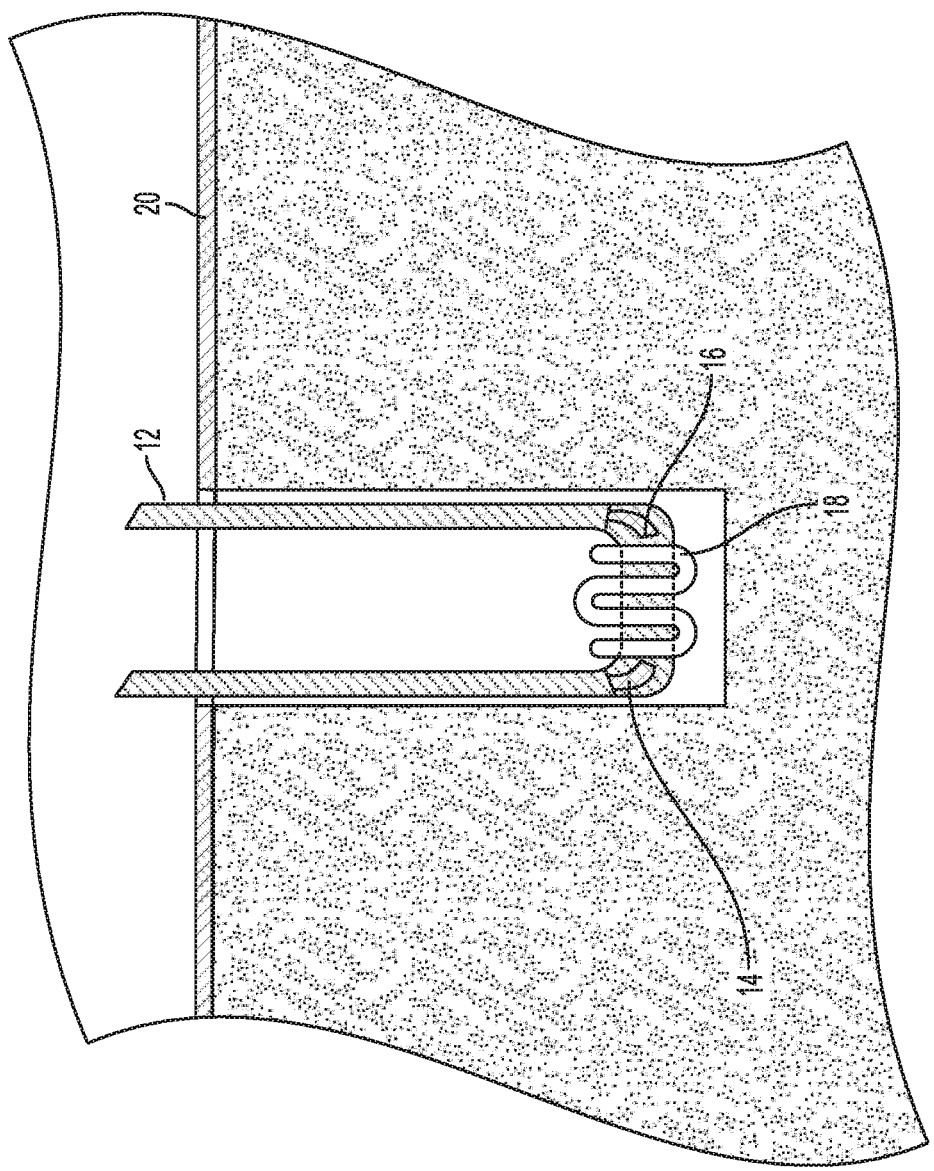
FIG. 4 is a schematic of a suture tape construct positioned in the bone of a subject after deployment.

Referring to FIG. 3, suture construct 10 with braided material 18 is positioned into a hole formed in bone 20 in the extended configuration. When the ends of fibrous filament 12 are pulled, braided material 18 will move to the deployed configuration of FIG. 4 by passing over protrusions 14 and 16 to an anchor knot, referred to as a Y-Knot® anchor knot between protrusions 14 and 16. As protrusions 14 and 16 abut against braided material 18 but do not allow passage of braided material 18 relative to suture fibrous filament 12 in the opposite direction, protrusions 14 and 16 prevent suture fibrous filament 12 from sliding relative to the y-knot formed by braided material 18. As a result, suture construct 10 may be used for a soft tissue to bone repair procedure, such as a double rotator cuff repair. Suture construct 10 thus allows for a soft tissue to bone repair using suture tape without the need for additional steps to secure against sliding as the suture tape of suture construct 10 is non-sliding with respect to braided material 18 that acts as the suture anchor.

In an alternative embodiment, similar to FIG. 3, the ends of braided material 18 are distally positioned in the extended configuration, while the ends of suture fibrous filament 12 are proximally positioned. When the ends of braided material 18 are located closer to the bone wall, they stick to the bone wall when the ends of suture fibrous filament 12 are pulled upward. Resistance provided by the bone wall against the ends of braided material 12 causes the portion of braided material 18 between protrusions 14 and 16 to compress and expand, filling the width of the bone hole.

Figure 5:
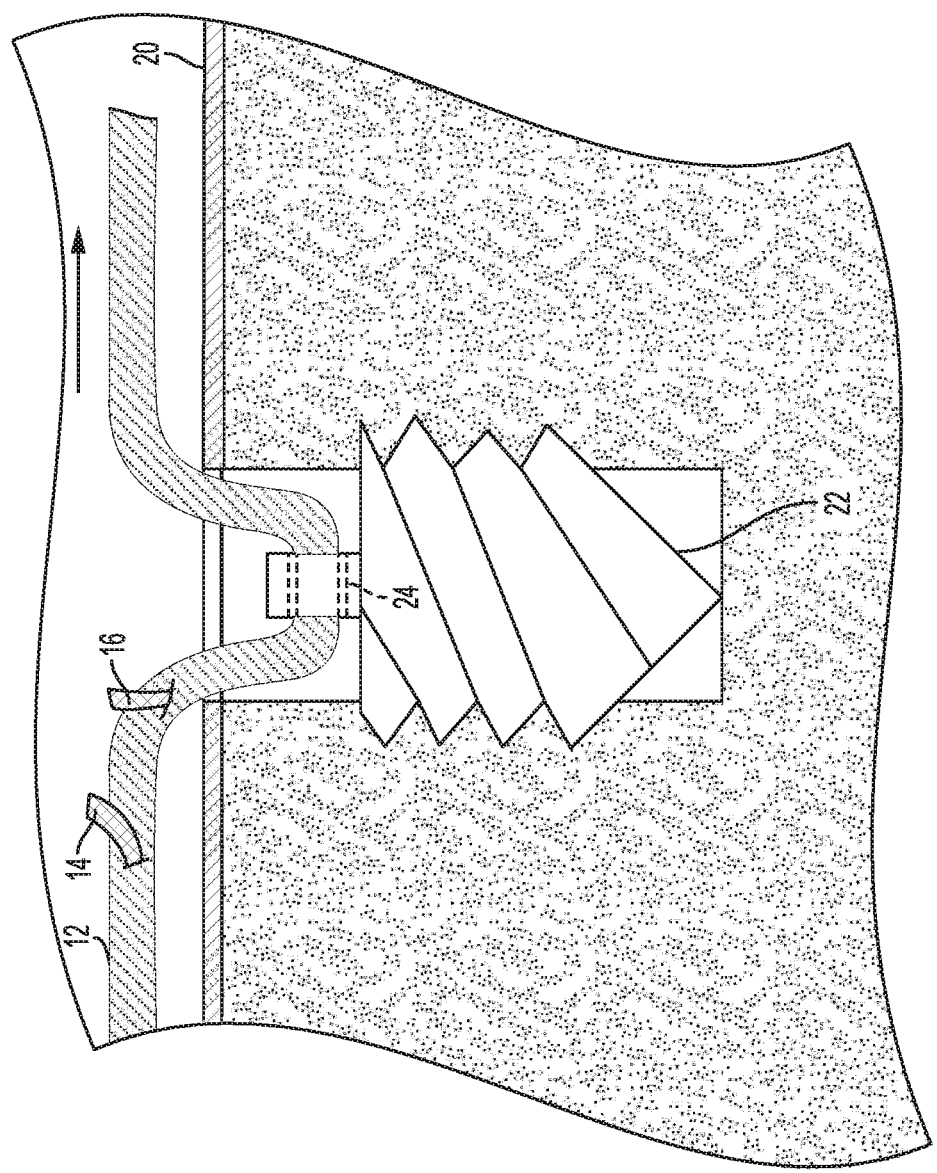
FIG. 5 is schematic of a suture tape construct used in connection with a threaded anchor prior to deployment.
Figure 6:
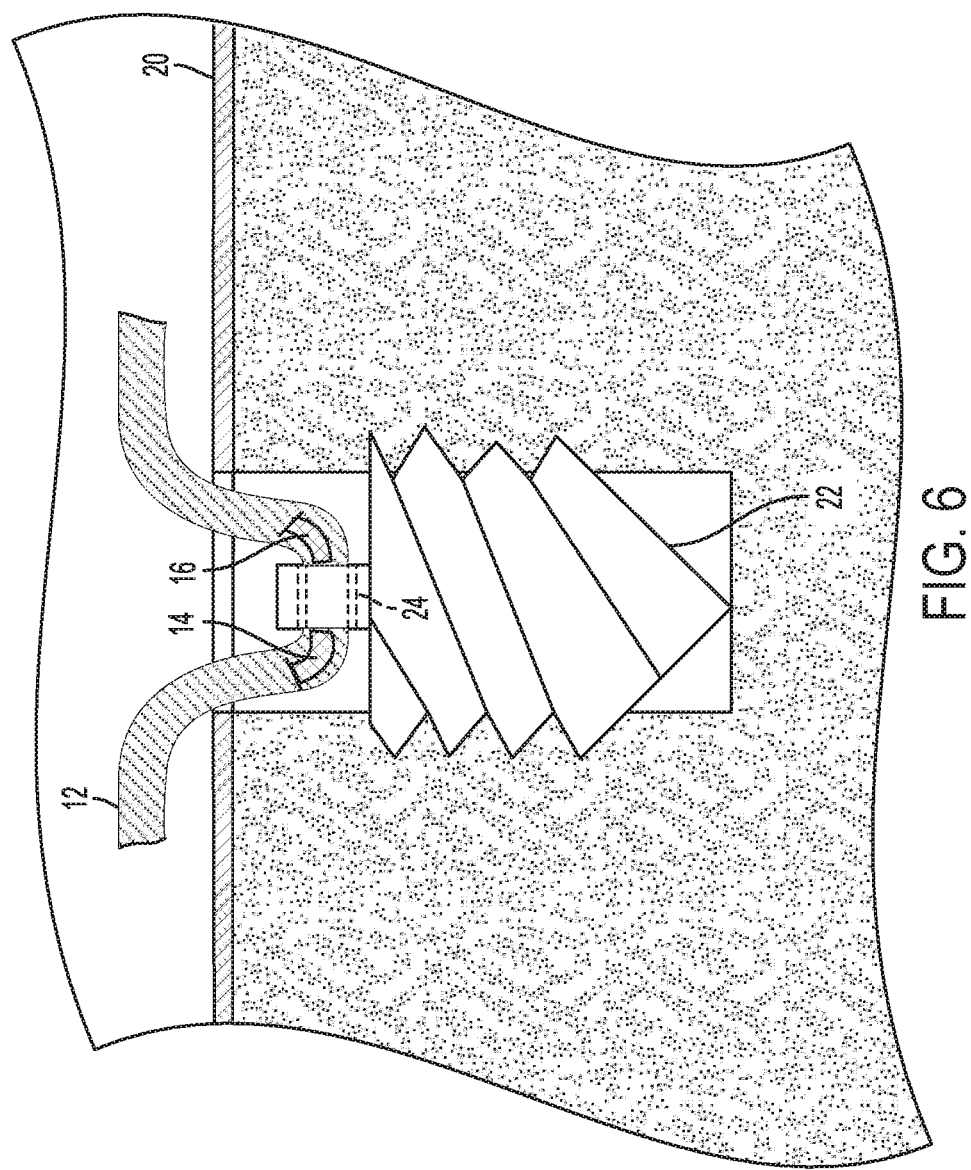
FIG. 6 is schematic of a suture tape construct used in connection with a threaded anchor after deployment.

Referring to FIG. 5, non-sliding suture construct 10 comprising a length of suture fibrous filament 12 and having a pair of protrusions 14 and 16 extending outwardly therefrom may also be used in combination with a threaded anchor 22 having an eyelet 24. In this embodiment, anchor 22 is first positioned in a bone 20, as seen in FIG. 5, with protrusions 14 and 16 positioned to one side of eyelet 24. Next, construct 10 is slid through eyelet 24 in one direction until one of protrusions 14 and 16 passes through eyelet 24, thereby capturing eyelet 24 between protrusions 14 and 16, as seen in FIG. 6.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A fibrous filament construct, comprising:
   a first section of fibrous filament extending from a first fibrous filament end to a second fibrous filament end;
   a pair of protrusions comprising a first protrusion and a second protrusion and extending from intermediate portions of the first section and spaced apart from each other to capture a suture anchor therebetween; and
   a second section including a plurality of folds, each of which includes a pair of legs and each leg includes a first inside surface and a second outside surface, wherein the second section extends along a longitudinal axis from a first second section end and a second section end, the second section includes a plurality of passing locations extending through each leg and through the first inside surface and the second outside surface of each leg at an angle to the longitudinal axis, wherein:
   the first section extends through each of the plurality of passing locations from the first inside surface to the second outside surface of each leg; and
   the second section is moveable from an un-deployed position where the second section extends beyond the pair of protrusions to a deployed position where the second section is captured between the pair of protrusions, wherein when the second section is in the deployed position, the pair of protrusions is configured to actively block the second section from moving from the deployed position to the un-deployed position, wherein when the second section is in the deployed position, the first protrusion abuts a second outside surface of a first leg of a first pair of legs of a first fold of the plurality of folds and the second protrusion abuts a second outside surface of a second leg of a second pair of legs of a second fold of the plurality of folds.

2. The construct of claim 1, wherein the fibrous filament of the first section is suture tape.

3. The construct of claim 1, wherein the second section is braided.

4. The construct of claim 1, wherein the second section is flat.

5. The construct of claim 1, wherein the protrusions comprise segments of suture woven into the fibrous filament of the first section and extending therefrom at an angle that only allows passage of the second section in one direction.

6. The construct of claim 1, wherein the thickness of the second section is greater in the deployed position as compared to the thickness of the second section in the un-deployed position.

7. The construct of claim 1, wherein the second section comprises a lumen and is tubular.

8. The construct of claim 7, wherein the lumen extends within the second section between the pair of protrusions.

9. The construct of claim 8, wherein a portion of the first section extends through the lumen of the second section.

10. The construct of claim 1, further comprising a threaded anchor having an eyelet through which the first section passes.

11. The construct of claim 10, wherein the first section is moveable from an un-deployed position where the eyelet is positioned along the first section outside of the pair of protrusions to a deployed position where the eyelet is captured between the pair of protrusions.

12. The construct of claim 1, wherein each of the protrusions of the pair of protrusions is configured to block the second section from moving back to the un-deployed position by abutting the second outside surface of a different one of the respective legs.

13. The construct of claim 1, wherein the fibrous filament construct consists essentially of one pair of protrusions.

* * * * *